United States Patent [19]

Van Doorn et al.

[11] 4,027,537

[45] June 7, 1977

[54] APPARATUS FOR SAMPLING A STREAM OF FIBERS AND THE LIKE

[75] Inventors: Donald W. Van Doorn, Columbus; Donald R. Lloyd, Midland, both of Ga.

[73] Assignee: Lummus Industries, Inc., Columbus, Ga.

[22] Filed: June 21, 1976

[21] Appl. No.: 698,108

[52] U.S. Cl. .............................. 73/421 R; 73/422 R
[51] Int. Cl.² ......................................... G01N 1/04
[58] Field of Search .................... 73/421 R, 422 R

[56] References Cited
UNITED STATES PATENTS

| 2,509,264 | 5/1950 | Cox | 73/422 |
| 3,987,678 | 10/1976 | Gable | 73/422 |

*Primary Examiner*—S. Clement Swisher
*Attorney, Agent, or Firm*—Jennings, Carter & Thompson

[57] ABSTRACT

Apparatus for sampling fibers which is simplified over previous apparatus for like purpose. A part of the fiber collecting chamber is movable to form a valve for admitting or excluding cotton; a part of the collecting chamber acts as dogs to hold the cotton in the sample chamber with each stroke of a platen; each stroke of the platen cleans the side walls of the collecting chamber; and means is provided for packaging the sample. The apparatus lends itself to automation so that it will collect a sample and eject and package the same after a predetermined number of strokes of the platen.

22 Claims, 6 Drawing Figures

APPARATUS FOR SAMPLING A STREAM OF FIBERS AND THE LIKE

This invention relates to apparatus for sampling a stream of fibers for the purpose of determining the average grade, quality, or various other characteristics of a given quantity of fibers.

Our invention relates more particularly to apparatus useful for sampling, at predetermined, desired intervals of time or increments of flow, a stream of fibers, either cotton or man-made, while passing along in a duct, for the purpose of permitting the grading, and thus the economic valuation thereof.

In the art to which our invention relates, particularly in the cotton ginning field, it is necessary that each bale of cotton be graded, namely, be inspected by a qualified person to determine many characteristics, features and conditions of the fiber. While there have been sampling devices, nevertheless up to this point in time and by and large such sampling has been done after the bales are completed and indeed, after the same have been placed in a warehouse. Furthermore, such samples heretofore when manually taken of necessity came from only two sides of the bale and experience shows that these samples are not fairly representative of the nature and quality of the fiber throughout the entire bale.

With regard to prior art sampling apparatus, the types known to us have been complicated, expensive to manufacture and not as reliable and efficient in operation as is desirable. Furthermore, such prior apparatus have been relatively large, require considerable power to operate and in general leave much to be desired, considering the kind of apparatus which must be efficient enough and reliable enough to operate as a part of a cotton ginning system.

With the foregoing in mind, one of the prime objects of our invention is to provide a sampler especially adapted for taking samples as desired from an airborne stream of fibers which shall be economical of manufacture, trouble-free in operation, require a minimum amount of power, and which shall have a capacity sufficient to permit its use in high capacity, modern-day ginning systems.

Our invention further comtemplates apparatus of the character designated in which all of the operating parts shall be fully enclosed, thus enhancing its safety and in which the parts are so constructed and operated as to produce a minimum amount of noise.

More specifically, our invention contemplates apparatus of the character designated which may be installed in an existing ginning system without major change therein, as well as being initially designed into such systems.

A more detailed object of our invention is to combine, in our apparatus, several of the functions and features of prior apparatus into single units. By way of example, a part of our fiber collection mechanism also serves as the dogs or retaining means to hold the compacted sample in its chamber; a further part of the collection system also functions as a valve either to admit the fiber into the collection space for sampling or to exclude the same. Still further, instead of using separate tramper and compacting members as in prior devices, in our apparatus the packer also acts as the tramper. This has the additional advantage of eliminating, as in the prior devices, the powered dogs and permitting the use of simple, spring actuated dogs which as before stated are a part of the collection chamber. In like fashion, and because of this last mentioned improvement, we have eliminated the power-actuated chocks heretofore required to hold the tramper platen in lowered position while the compacting member in the prior apparatus compressed the fiber.

Our invention is further characterized by the complete absence of revolving drum-doffing cylinder condensers together with the attendant mechanism required physically to move the doffed sample into the compaction chamber.

Another object of our invention is to provide apparatus of the character designated in which the collection chamber in made of foraminous material such as perforated metal and in which the combined tramping and compacting platen, on each stroke, serves to doff the side walls of fiber clinging thereto, whereby our apparatus is self-cleaning, thereby maintaining its efficiency and making its operation more trouble-free.

A further object of our invention is to provide lint sampling apparatus which lends itself readily to the provision of safety controls therefor and which may readily be automated into a complete system, such for instance, as a cotton ginning system.

DESCRIPTION OF THE DRAWINGS

Apparatus illustrating features of our invention is shown in the accompanying drawings, forming a part hereof, in which:

FIG. 1 is a diagrammatic and schemmatic view illustrating our invention in a lint system or the like;

Figure 1:
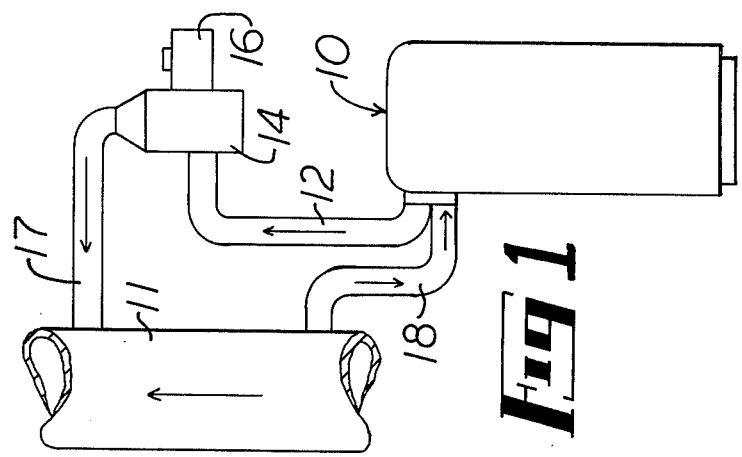

Referring now to the drawings for a better understanding of our invention it will be understood that our improved apparatus indicated generally by the numeral 10 is adapted for incorporation in a system which is handling the lint to be sampled such for instance as a cotton gin system. In cotton ginning systems there is a lint flue 11 which generally receives an airborne stream of lint cotton from a plurality of gins and which leads to a condenser placed ahead of a baling press. At 12 we show a conduit leading from an outlet opening 13 of our improved apparatus to the inlet of a fan 14. The fan may be powered by a motor 16 and its outlet is connected through a conduit 17 back to the lint flue 11. At 18 we show a conduit which is also connected to the lint flue 11 and to the inlet opening 19 of our improved apparatus.

From what has just been described it will be seen that the fan 14 induces a flow of lint through the conduit 18, into our improved apparatus 10, where the sample of lint is collected and packaged as will be explained, the air returning through the conduit 12 and 17 to the lint flue 11. Also, as will be understood as the description progresses when our apparatus is not actually sampling, airborne stream of lint bypasses through conduit 18, into our improved apparatus 10, but not through the sampling portions thereof, out through conduit 12 and thence is returned to the lint flue through conduits 17.

Figure 2:
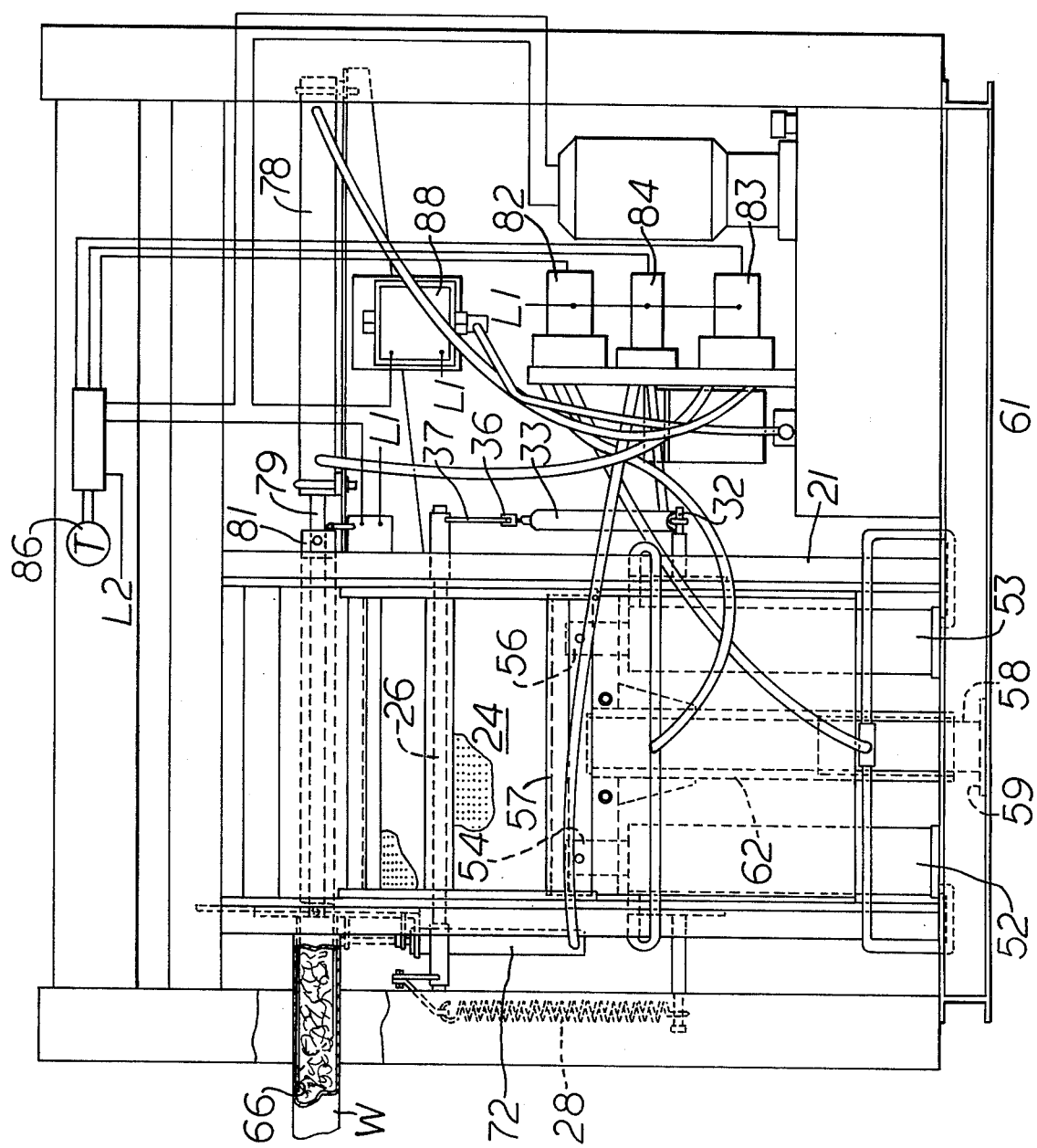
FIG. 2 is a side elevational view with certain parts diagrammatically shown thereon, and certain parts being broken away and in sections.

Referring now particularly to FIG. 2 our improved apparatus comprises a main housing 21, in the upper portion of which we provide the mechanism for securing the sample and packaging the same and in a lower portion of which we provide certain operating mechanisms.

Figure 3:
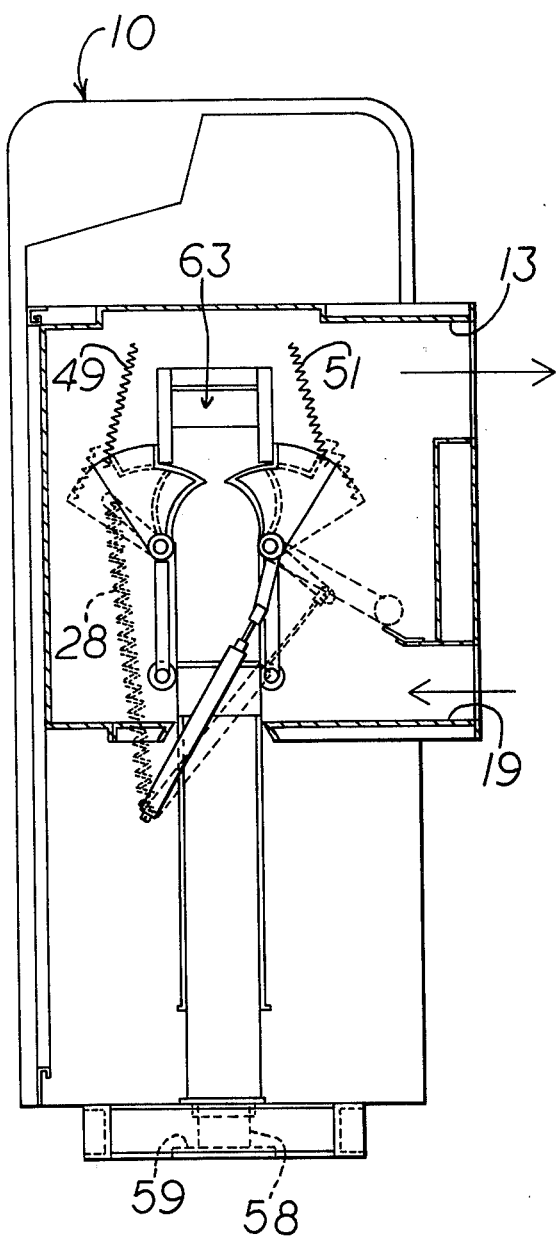
FIG. 3 is a rear elevational view with certain parts broken away and in section.
Figure 4:
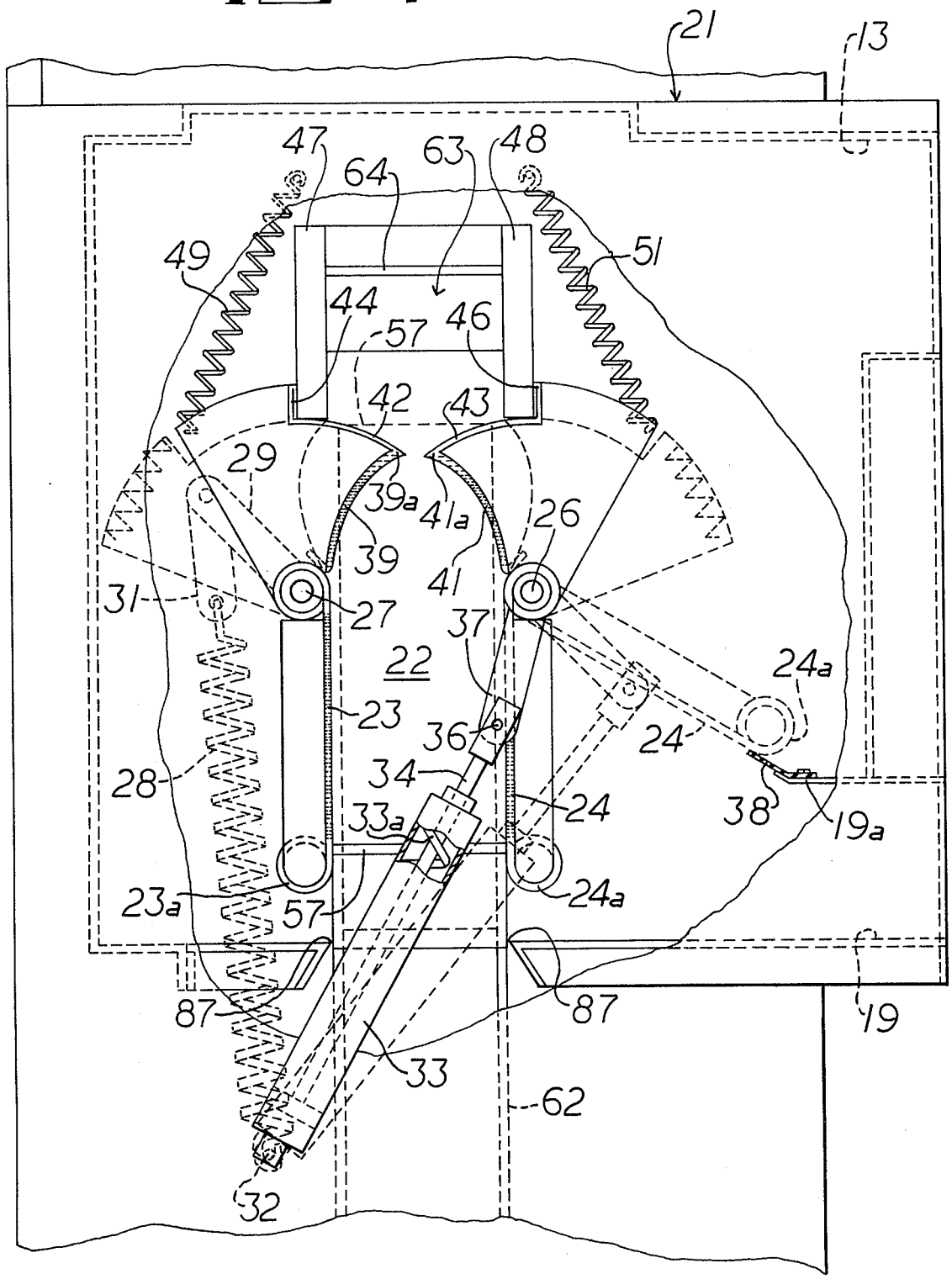
FIG. 4 is an enlarged detail view corresponding to a portion of FIG. 3.

Referring now to FIGS. 3 and 4 we show in both instances in full lines the position of the apparatus when the lint, in an airborne stream, from conduit 18 simply enters the opening 19 and exits the opening 13 in the conduit 12 to be returned through the fan and conduit 17 to the flue. In other words, the full line position shows the non-collecting position of the parts in both FIGS. 3 and 4.

The collecting chamber proper is indicated generally by the numeral 22. As shown, this chamber is defined by a pair of perforated plate walls 23 and 24. The wall 24 is mounted for rotation on a shaft 26 and the wall 23 is mounted for rotation on a shaft 27. The wall 23 is urged with its free end 23a into the full line position shown in FIG. 4 by means of a spring 28 which is connected to an arm 29 through a link 31. In other words, in normal position the wall 23 is in the full line position shown.

The wall 24 is adapted, during the operation of the apparatus, to move from the full line position of FIG. 4 to the dotted line position thereof. That is to say, at 32 we show the pivotal mounting of the non-piston rod end of a fluid pressure cylinder 33. The piston rod 34 of the cylinder is connected at 36 to a link 37 which in turn is made fast at its other end to the shaft 26. When the fluid is admitted to the lower end of the cylinder 33 the wall 24 moves with its free end 24a on top of and in sealing relation to a flap-type gasket 38 which is mounted at the end of the upper wall forming the inlet 19. The piston rod is biased inwardly by a spring 33a carried inside the cylinder 33.

Pivotally mounted for movement about the shaft 27 is an arcuate shaped perforated end wall 39 for chamber 22. In similar fashion, there is an arcuate, perforated end wall 41 pivotally mounted for rotation about shaft 26. Each of these arcuate sections carry imperforate plates 42 and 43 and the plates have stop members 44 and 46 adapted to engage respective frame members 47 and 48 forming parts of the sample chute as will presently be explained. The arcuate sections 39 and 41 are held resiliently in the full line position shown in FIG. 4 by means of springs 49 and 51.

Considering FIG. 2, mounted in the bottom of the apparatus is a pair of spaced fluid pressure cylinders 52 and 53. The piston rods 54 and 56 of the cylinders 52 and 53 carry a platen 57. The platen 57 is a rectangular member whose width is substantially equal to the width between the walls 23 and 24 as shown in FIG. 4 when in their lowered position. The platen is substantially the length of the housing. Thus, the platen 57 forms a movable bottom for the collection chamber 22.

The platen 57 is guided in its vertical movement, by means of a centrally disposed column 58. The column 58 has a base 59 which is secured to a base frame member 61 of the frame of the apparatus. Surrounding the column 58 is a sleeve 62. The platen 57 is secured to the upper end of the sleeve.

From what has been described so far it will be seen that when fluid is admitted to the bottom ends of the cylinders 52 and 53 the platen moves upwardly, between the walls 23 and 24 and, due to the inward biasing of the springs 49 and 51 on the arcuate walls 39 and 41, the platen can proceed upwardly, moving those last mentioned members to the dotted line positions shown in FIG. 4.

Mounted above the members 39 and 41 is a sample collecting trough or accumulating section indicated generally by the numeral 63. This trough member comprises an upper, horizontal plate 64 which is secured at its end to the longitudinally extending frame members 47 and 48, these members forming an inverted trough into which the cotton collected in chamber 22 may be pushed by the platen as will be explained.

Extending outwardly from a side wall of the frame is a chute 66 through which the collected sample is discharged as will appear. The chute 66 is in communication at its inner end with an opening 67 in the side wall of the apparatus.

Figure 5:
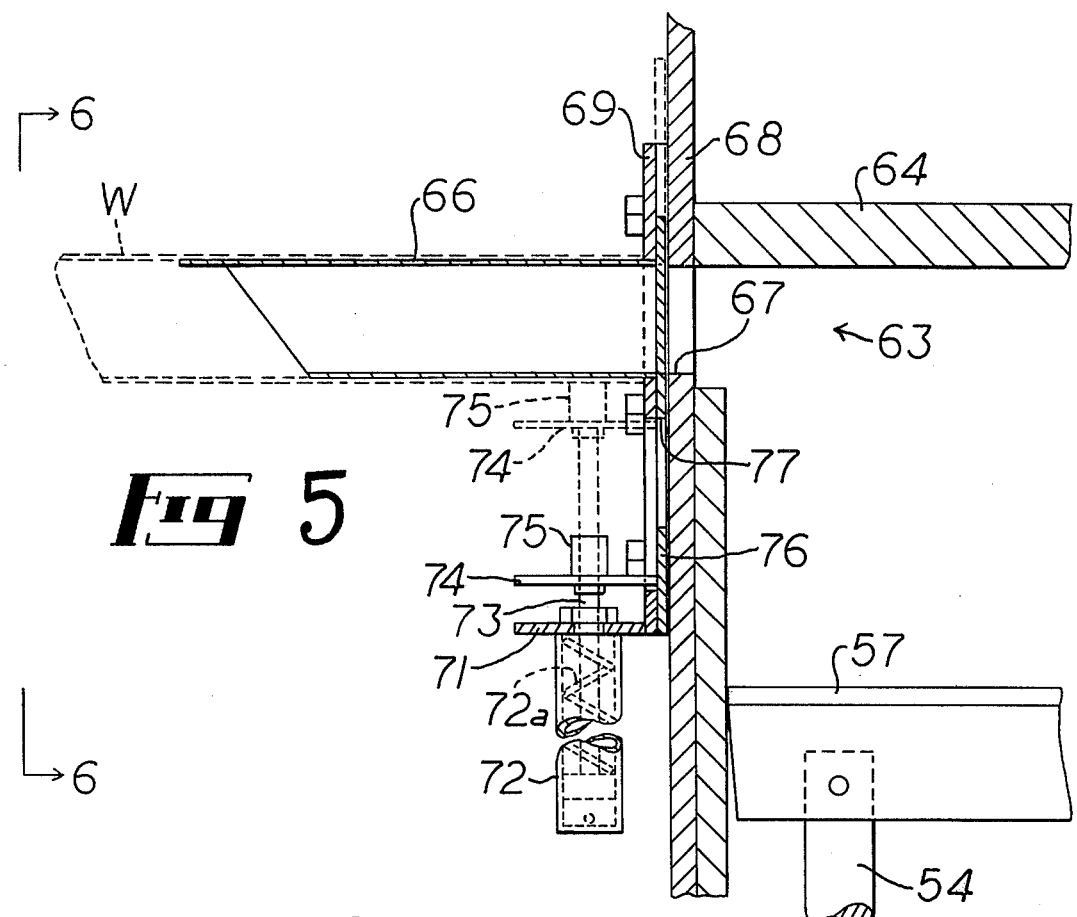
FIG. 5 is a detail sectional view taken generally along 5—5 of FIG. 6 and illustrating the sample chute and cut-off plate for closing the chute; and, FIG. 6 is a detail view taken generally along line 6—6 of FIG. 5.
Figure 6:
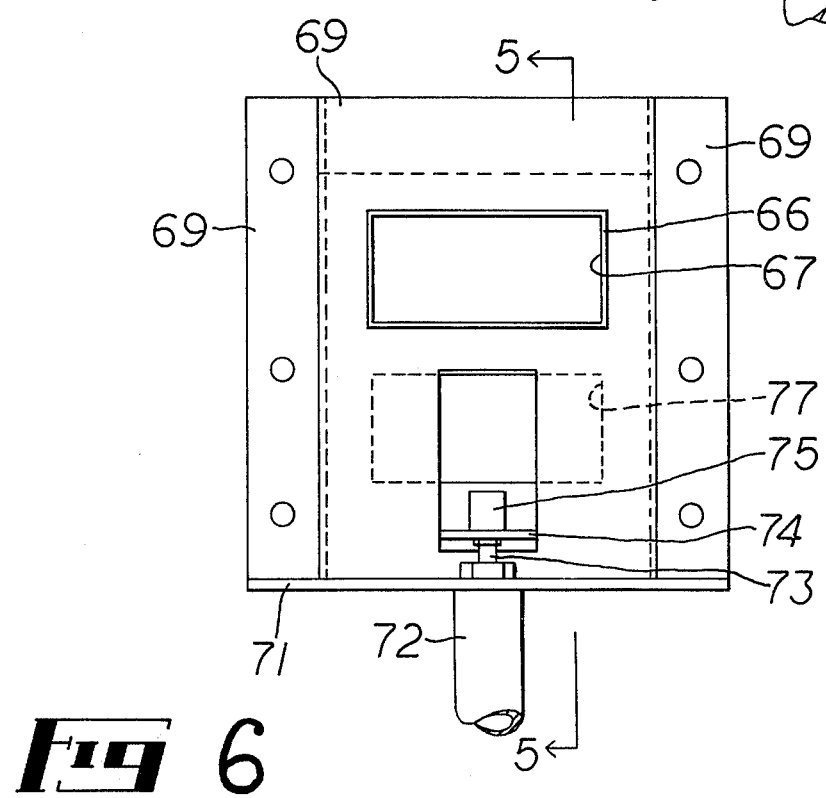

An L-shaped bracket having one vertical bracket 69 is secured in spaced relation to the side plate 68 and has its horizontal leg 71 extending outwardly as illustrated in FIG. 5. Secured to the leg 71 of the bracket is a fluid pressure cylinder 72. The piston rod 73 of the cylinder 72 is connected to an outstanding plate 74. The inner end of the plate 74 is secured to a slide 76. The slide 76 has an opening 77 therein adapted, when the parts move to the upper, dotted position shown in FIG. 5, to establish communication between the chute 66 and the collecting trough 63. The piston rod 73 of cylinder 72 is biased inwardly of the cylinder by a spring 72a carried inside the cylinder.

Carried by the framework is a horizontally disposed double-acting fluid pressure cylinder 78. The piston rod 79 of cylinder 78 carriers a platen 81 which is adapted, as will be explained, to push the sample of cotton which has been collected and is held by the platen 57 in the trough 63 to the left as viewed in FIG. 2, into the collection chute 66 where it may be bagged and disposed of. Further, the piston rod 73 carries a holding member such as a pad of rubber 75 adapted as will appear to hold a paper wrapper W on the chute 66 while it is being filled with the sample.

With the foregoing in mind the operation and advantages of our invention may now be more fully explained and understood. First, it will be understood that the hydraulic cylinders 52 and 53 are under control of a solenoid valve 82 so that fluid may be admitted selectively and simultaneously to the upper and lower ends thereof. The cylinder 78 is under control of a solenoid valve 83 so that fluid under pressure may be admitted selectively to opposite ends thereof. Finally, cylinders 72 and 33 are under control of a solenoid valve 84 so that fluid under pressure may be admitted to the lower ends thereof, simultaneously.

With the parts in the full line positions of FIGS. 3 and 4, and with the fan 14 in operation a sample of the airborne lint from the flue 11 is passed continuously from conduit 18, through the inlet opening 19, out the outlet opening 13 and thence to the conduit 12, fan 14 and is returned to the conduit 11 through the conduit 17. Whenever it is desired to take a sample the first action is to energize cylinder 33, moving the movable wall 24 from the full line position of FIG. 4 to the dotted line position thereof. The end 24a of the wall then is in sealing contact with the flexible seal member 38. In this position of the parts the airborne stream of lint enters the opening 19 and collects on the walls 24, 23 and 39 and 41, the air bypassing through the perforated parts and returning out of the outlet opening 13 to be returned to the line flue. In this position of the parts it will be understood that the cylinder 72 is holding the opening 67 closed so that the air and lint will not escape through the opening 67.

After the wall 24 has stayed in the dotted line position for a given length of time as determined, for instance, by a timer 86, cylinder 33 is deactivated and spring 33a therein returns the piston to the lower end of that cylinder. This then brings the lint laden inner surface of wall 24 back to the full line position of FIG. 4.

The timer now activiates cylinders 52 and 53, moving the platen upwardly. It will be noted that the platen is in scrapping, close fitting relations to the inner surfaces of walls 23 and 24 and hence purges these walls of lint clinging thereto. Continued upward movement of the platen 57 engages and scraps the inner surfaces of the walls 39 and 41 clear of lint. The springs 49 and 51 permit the arcuate sections 39 and 41 to move outwardly, to permit the piston to move up into the chamber 63, but the platen 57 does not travel far enough to move past the points or ends 39a or 41a of the respective plates 39 and 41, these remaining engaged with the sides of the platen. In accordance with the way the timer is set the cylinders 52 and 53 may now be energized from their upper ends, lowering the platen. It will be noted that as soon as the upper surface of the platen clears the points 38a and 41a these members move back in into the full line position of FIG. 4, forming dogs which support the cotton which has just been moved upwardly above said members 39 and 41. The timer now activates cylinder 33 again, whereupon additional cotton is deposited and the cycle repeats itself. Finally, in response to the timer the platen remains in its uppermost position with a full sample of cotton in the chamber 63. The timer now activates cylinder 78 to move the platen 81 thereof from right to left as viewed in FIG. 2, with the platen still raised, and simultaneously the cylinder 72 has been activated or energized from its bottom end, moving the plate 76 upwardly so that the opening 77 thereof comes into alignment with opening 67. The sample of cotton is now extruded into the tube 66. A paper envelope type of packaging material W is slipped over the tube, so that as the platen 81 moves from right to left as viewed in FIG. 2 the slug or sample of cotton is pushed far enough out of the chute 66 to be caught in the packaging material W. The member 75 engages the package W against the underside of chute 66 and prevents it from slipping off the tube 66 while the packaging material W is being loaded.

From the foregoing it will be seen that we have devised an improved sampler for taking samples of lint cotton and the like and collecting the same. Our invention readily lends itself to automation as will be apparent to those skilled in the art and its cycles may be controlled. Our invention is characterized by the absence of condensers of the rotary drum type and the absense of mechanically actuated dogs, as separate elements, to hold the cotton in place with each stroke of the tramper or packing member. In other words, the curved sections 39 and 41 serve dual functions, namely, they are part of a collecting chamber and at the same time serve as dogs to hold the cotton in position above the platen.

Another feature of our invention also is the fact that by providing small openings 87 at the places indicated in FIG. 4 of the drawings we always induce into the housing of our apparatus a small flow of air, thus preventing any loss of lint, making the apparatus extremely clean in operation.

A pressure switch 88 may be employed to stop the collecting strokes of the platen when the pressure exerted by the platen on the specimen reaches a predetermined value. Suitable controls associated with such switch then cause energization of cylinder 78 to eject the compacted sample.

The system is operated so as to maintain in the interior of the housing 21 negative pressure on the order of 5 to 10 inches, water gauge, thus to induce a flow of air through the openings 87.

Our invention has proven to be extremely practical and efficient in operation and the elimination of the rotary type condensers for this type of apparatus has removed one of the major problems involved in the same. It will be noted that our apparatus is self-cleaning in the sense that each stroke of the platen 57 scavenges the inner walls of the entire collection chamber of lint which has been collected thereon when the parts are in sample collecting position.

While we have shown our invention in but one form, it will be obvious to those skilled in the art that is is not so limited but is susceptible of various changes and modifications without departing from the spirit thereof.

What we claim is:

1. In apparatus adapted to sample fiber-like material while in an airborne stream,
    a. a sample collecting chamber,
    b. said chamber having at least one wall pervious to air and substantially impervious to the material to be collected,
    c. means to admit the airborne material to the chamber comprising a movable wall section of the collecting chamber disposed in one position to direct the airborne stream into the chamber and in another position to close the chamber, whereby the airborne stream may be selectively passed into or caused to by-pass the collecting chamber.
    d. a reciprocating platen in the chamber, and
    e. means to remove the material from the apparatus as a compacted sample.

2. Apparatus as defined in claim 1 in which the platen on its compacting stroke wipes the collected material from said air-pervious wall.

3. Apparatus as defined in claim 1 in which said movable wall section is formed of material pervious to air and impervious to the material to be collected, whereby when in open position said wall section serves as a part of the collection chamber.

4. Apparatus as defined in claim 3 in which said wall section when closed is disposed for material collected thereon to be removed by the platen.

5. Apparatus as defined in claim 1 in which the platen is adapted to remove material from the chamber and in which there are movable material holding dogs adjacent the chamber disposed to hold the removed material upon retraction of the platen from its material removing position.

6. Apparatus as defined in claim 5 in which the dogs are plate-like members, and means pivotally mounting the dogs to move apart as the platen removes the material from the chamber and to move toward each other upon retraction of the platen relative to the chamber.

7. Apparatus as defined in claim 1 in which a substantially air-tight housing surrounds the collecting chamber, means associated with the housing to admit the airborne material into the chamber, and means to maintain the interior of the housing under sub-atmospheric pressure.

8. Apparatus as defined in claim 7 in which the sub-atmospheric pressure in the housing is on the order of 5 to 10 inches on the water gauge.

9. Apparatus as defined in claim 7 in which there are openings into the housing located for streams of air passing through said openings to cleanse the side surfaces of the platen.

10. Apparatus as defined in claim 7 in which there is power means for operating the platen and in which there are openings into the housing for streams of air to pass therethrough, and means to direct the streams of air over said power means.

11. Apparatus as defined in claim 1 in which there is a fiber accumulating section adjacent the fiber collecting chamber into which the platen moves the fiber from the chamber, there being an opening from said fiber accumulating section to atmosphere, a movable closure for the opening, means to move the closure to a position to uncover said opening, and means to discharge the fiber in the accumulating section through said opening.

12. Apparatus as defined in claim 11 in which the material in the accumulating section is adapted to be placed in a package, and means associated with said closure effective upon movement of the closure to uncover said opening to hold a package in position to receive said material.

13. Apparatus as defined in claim 1 in which there is means effective to stop further collecting strokes of the platen when the pressure exerted on the material by the platen reaches a predetermined value.

14. Apparatus as defined in claim 1 in which there is means to position the platen above the collecting chamber during times when no sample is being taken from said stream.

15. In apparatus adapted to sample fiber-like material while in an airborne stream,
   a. a sample collecting chamber,
   b. said chamber having at least one wall pervious to air and substantially impervious to the material to be collected,
   c. means to admit the airborne material to the chamber comprising a movable wall section of the collecting chamber disposed in one position to direct the airborne stream into the chamber and in another position to close the chamber, whereby the airborne stream may be selectively passed into or caused to by-pass the collecting chamber,
   d. a reciprocating platen in the chamber,
   e. a sample accumulating section located adjacent an end of the collecting chamber and into which the platen moves the sample collected in the chamber, and
   f. means associated with the sample accumulating section to remove the sample therefrom.

16. Apparatus as defined in claim 15 in which the means to remove the accumulated sample comprises a second platen disposed to push the accumulated sample from the sample accumulating section.

17. Apparatus as defined in claim 16 in which the second platen is mounted for reciprocation generally normally of the path of movement of the first named platen.

18. In apparatus adapted to sample fiber-like material while in an airborne stream,
   a. a sample collecting chamber,
   b. said chamber having at least one wall pervious to air and substantially impervious to the material to be collected;
   c. means to admit the airborne material into the chamber,
   d. a reciprocating platen in the chamber movable through an end thereof to remove material from the chamber,
   e. sections of the walls of the chamber adjacent the end through which the material is removed being pivoted and disposed to act as dogs to hold the material removed from the chamber by the platen, and
   f. means to remove the material from the apparatus as a compacted sample.

19. Apparatus as defined in claim 15 in which the means to remove the sample from the accumulating section comprises an opening in a wall of said section, a closure member for said opening, and means to remove the closure member during removal of the sample.

20. In apparatus adapted to sample fiber-like material while in an airborne stream,
   a. a sample collecting chamber,
   b. said chamber having at least one wall pervious to air and substantially impervious to the material to be collected,
   c. means to admit the airborne material to the chamber comprising a movable wall section of the collecting chamber disposed in one position to direct the airborne stream into the chamber and in another position to close the chamber whereby the airborne stream may be selectively passed into or caused to by-pass the collecting chamber,
   d. a reciprocating platen in the chamber,
   e. means to remove the material from the apparatus as a compacted sample including an opening through which the sample is removed, and
   f. means to maintain the opening closed except during sample removal.

21. In apparatus adapted to sample fiber-like material while in an airborne stream,
   a. a substantially air-tight housing having inlet and outlet openings for the said airborne stream,
   b. a sample collecting chamber in the housing,
   c. said chamber having at least one wall pervious to air and substantially impervious to the material to be collected,
   d. said chamber being open at one end and substantially closed at its opposite end,
   e. means to admit the airborne material into the chamber,
   f. a reciprocating platen forming an impervious closure for the open end of the chamber and movable to discharge the material from the chamber, and
   g. means to remove the material from the apparatus as a compacted sample.

22. Apparatus as defined in claim 21 in which the means to remove the material as a compacted sample comprise an accumulating section located for the platen to deliver thereto the material collected in the collection chamber, a second reciprocating platen associated with the accumulating section and disposed to remove the accumulated material from the apparatus.

* * * * *